(12) United States Patent
McCarthy et al.

(10) Patent No.: US 11,806,254 B2
(45) Date of Patent: *Nov. 7, 2023

(54) PROSTHESIS SUSPENSION LINER SEALING CAP AND PROSTHESIS SUSPENSION SYSTEM

(71) Applicant: Blatchford Products Limited, Basingstoke (GB)

(72) Inventors: Joseph Ronald McCarthy, Fareham (GB); Alan McDougall, Hampshire (GB); Ana Isabel Gallego Murillo, Greater London (GB)

(73) Assignee: BLATCHFORD PRODUCTS LIMITED, Hampshire (GB)

( * ) Notice: Subject to any disclaimer, the term of this patent is extended or adjusted under 35 U.S.C. 154(b) by 158 days.

This patent is subject to a terminal disclaimer.

(21) Appl. No.: 17/461,177

(22) Filed: Aug. 30, 2021

(65) Prior Publication Data

US 2021/0386564 A1 Dec. 16, 2021

Related U.S. Application Data

(63) Continuation of application No. 16/335,768, filed as application No. PCT/GB2017/052863 on Sep. 25, 2017, now Pat. No. 11,103,370.

(30) Foreign Application Priority Data

Sep. 23, 2016 (GB) ...................... 1616241

(51) Int. Cl.
*A61F 2/78* (2006.01)
*A61F 2/80* (2006.01)
*A61F 2/60* (2006.01)

(52) U.S. Cl.
CPC .............. *A61F 2/7812* (2013.01); *A61F 2/78* (2013.01); *A61F 2/60* (2013.01);
(Continued)

(58) Field of Classification Search
CPC .............. A61F 2/7812; A61F 2002/802; A61F 2002/807; A61F 2002/7831; A61F 2002/7875; A61F 2/80; A61F 2220/0025
See application file for complete search history.

(56) References Cited

U.S. PATENT DOCUMENTS

| | | |
|---|---|---|
| 7,235,108 B2 | 6/2007 | Carstens |
| 2004/0243251 A1 | 12/2004 | Carstens |

(Continued)

FOREIGN PATENT DOCUMENTS

| | | |
|---|---|---|
| WO | 2014032802 A1 | 3/2014 |
| WO | 2014205403 A1 | 12/2014 |

OTHER PUBLICATIONS

Int'l Search Report and Written Opinion dated Dec. 19, 2017 in Int'l Application No. PCT/GB2017/052863.

(Continued)

*Primary Examiner* — Javier G Blanco
(74) *Attorney, Agent, or Firm* — Panitch Schwarze Belisario & Nadel LLP

(57) ABSTRACT

A prosthesis suspension system comprises a socket for receiving a residual limb, a locking liner having a locking pin for attaching the liner to the socket and a sealing cap disposed between the locking line and the socket. The system further comprises a gap between a skirt of the sealing cap and an interior wall of the socket in which the skirt of the sealing cap is able to move between first and second positions.

10 Claims, 3 Drawing Sheets

(52) U.S. Cl.
CPC ............ *A61F 2002/7831* (2013.01); *A61F 2002/7875* (2013.01); *A61F 2002/802* (2013.01); *A61F 2002/807* (2013.01); *A61F 2220/0025* (2013.01)

(56) References Cited

U.S. PATENT DOCUMENTS

| | | |
|---|---|---|
| 2007/0005149 A1 | 1/2007 | Egilsson et al. |
| 2011/0022184 A1* | 1/2011 | Slemker .............. A61F 2/80 623/36 |
| 2012/0109336 A1 | 5/2012 | Laghi |
| 2012/0191217 A1 | 7/2012 | Mackenzie |
| 2012/0191218 A1 | 7/2012 | McCarthy |
| 2014/0005800 A1 | 1/2014 | Kelley et al. |
| 2015/0202060 A1 | 7/2015 | Muller et al. |

OTHER PUBLICATIONS

Search Report dated Feb. 20, 2017 in GB Application No. GB1612414.
Office Action dated Sep. 3, 2020 in U.S. Appl. No. 16/335,768 by McCarthy.

* cited by examiner

PROSTHESIS SUSPENSION LINER SEALING CAP AND PROSTHESIS SUSPENSION SYSTEM

CROSS-REFERENCE TO RELATED APPLICATIONS

This application is a Continuation of co-pending U.S. patent application Ser. No. 16/335,768, having a filing date of May 24, 2019 under 35 U.S.C. § 371(c), which is a Section 371 of International Application No. PCT/GB2017/052863, filed on Sep. 25, 2017, which claims priority from Application No. 1616241.4, filed on Sep. 23, 2016 in the United Kingdom. The entire contents of these applications are incorporated herein by reference in their entirety.

TECHNICAL FIELD

The present invention relates to a prosthesis suspension system and a liner sealing cap for such a system. In particular, the present invention relates to a sealing cap for a porous suspension liner forming part of a reduced pressure lower limb prosthesis suspension system.

BACKGROUND TO THE INVENTION AND PRIOR ART

A prosthesis can be attached to a residual limb in the following manner. A hollow hard socket is custom made to accommodate the shape of the residual limb. The socket includes means for attaching the prosthesis to the socket. Before inserting the residual limb into the socket a soft flexible liner is typically donned on the residual limb to serve as an interface between the residual limb and the socket. The liner is typically made from an air impermeable material such as silicone.

There are two types of suspension liners, namely locking and non-locking (often referred to as cushion) liners. In addition to performing a cushioning function, locking liners also provide a mechanism for conveniently securing the liner to a socket. To achieve this, locking liners include an umbrella at their distal end. The umbrella is either attached to a distal end of the liner or is partially or fully embedded within the material of the liner. Extending distally from the umbrella is a boss. The boss includes an internally threaded bore for receiving a pin. Once in place the pin is fed through a corresponding hole in a socket and locked thereto. In this way the socket is firmly attached to the liner by means of the pin. An example of such a locking liner is described in WO 95/31160.

An intimate fit is required between the residual limb, the liner and the socket. This close fit is required to prevent relative motion between the socket and liner and the residual limb, to prevent irritation of the skin and other soft tissue of the residual limb. The intimate fit better distributes forces on the residual limb when weight is applied to the prosthesis via the socket. For a lower limb prosthesis, this will occur when the prosthesis is in contact with ground, for example when standing and during the stance phase of the gait cycle.

Since the residual limb is surrounded by the liner, when sweat is secreted by the residual limb it is captured within the liner. Furthermore, since the amputee must expend a heightened effort in the residual limb, the limb is prone to produce increased volumes of sweat. When sweat is secreted onto the skin it can act as a lubricant and reduce adhesion of the limb to the liner. This reduced adhesion leads to a number of problems, such as relative movement between the residual and prosthetic limbs, reduced control and proprioception, increased energy expenditure leading to further sweating and fatigue, and chafing. The moist and warm environment resulting from the build-up of sweat within the liner also provides an ideal breeding ground for pathogens.

To address this problem liners have been developed which allow removal of sweat, air and other fluids from the liner-residual limb interface, typically using air expulsion arrangements. Air expulsion achieved as a result of the intimate fit, typically via a one-way valve, is used to contribute to the formation of a reduced pressure/(partial) vacuum between the liner and the socket so that the prosthesis remains suspended from the residual limb. For a lower limb prosthesis this will occur during the swing phase of the gait cycle, when the limb is not in contact with the ground. Hence, the presence of a low pressure/vacuum between the socket and the residual limb-liner combination is a desirable feature of such prostheses.

A number of methods have been used to maintain a reduced pressure within the socket during the swing phase. For example, our patent application published as GB-A-2486817 describes a vacuum assisted suspension device for a prosthesis comprising an air impermeable socket shaped to receive a limb portion. The socket has a peripheral edge and includes an evacuation port and a non-return valve associated with the evacuation port. The evacuation port and return valve are arranged to maintain a vacuum between the socket and the limb portion when the latter is received by the socket. The device includes a sleeve which spans the peripheral edge of the socket and the limb portion. When air is evacuated/expelled from the socket via the evacuation port the sleeve acts as a seal.

As a further example, our patent application published as EP-A-2254526 describes a vacuum-assisted liner system for the socket of a limb prosthesis which secures the prosthesis to a residual body portion. The system includes a flexible liner made of an impermeable material, at least a distal part of the liner being porous to allow the transport of air and fluid directly away from the residual body portion to the outer surface of the liner. A fabric distribution layer is located over the liner and between the liner and the socket to allow transmission of such extracted air and fluid laterally over the liner to an evacuation port in the socket.

There are other known methods of sealing the cavity between the exterior of the suspension liner and the interior of the socket. For example the liner may include peripheral seals which bear on the interior wall of the socket to form an airtight seals. US-A1-2011/0264239 describes a suspension liner sleeve having an elongate, generally conical body. The liner sleeve includes a plurality of resilient seal elements protruding radially from the liner sleeve outer surface. A pair of adjacent annular recesses may be located above and below each of the seal elements. When the limb and liner are inserted into the socket the seal deforms against the force exerted by the socket into its associated annular recess and seals against the interior of the socket. A number of alternate seal designs are described in that document. Other prior art publications include U.S. Pat. Nos. 6,726,726, 6,645,253, WO-A-01/070147 and WO-A-02/067825.

US-A-2004/0243251 describes a prosthetic socket having an aperture at its distal end fitted with a seal that is configured in such a way that a tension applied to the said prosthetic socket produces a self-generating force at the seal as a result of the atmospheric external pressure increasing the sealing action provided by the sealing lip. The seal may be affixed to the prosthetic socket and/or to a liner, the sealing edge always being radially nearer the aperture to be sealed than is the root of the sealing lip.

WO-A-2014/205403 describes a moisture management liner device for a prosthetic socket which may include an elongate, cup-shaped, elastomeric member and multiple fluid transport strips. The elastomeric member may include a first material and may extend from an open proximal end to a substantially closed distal end.

US-A-2012/109336 describes a prosthesis suspension assembly comprising: a prosthetic socket having an open proximal end and a closed distal end and an interior surface, an interface or liner for receiving the residual limb and fittingly received in the socket, a distal outer surface of the liner comprising a porous or continuously cavitated, compressible material and a proximal outer surface comprising an elastomeric material, a suspension sleeve which seals against the proximal outer surface of the liner and a proximal outer surface of the socket, and a locking pin connected to a distal end of the liner and lockingly retained in a hole in the distal end of the socket and including an air passage therethrough with a one-way valve therein for permitting the exit of air from an interstitial volume occupied buy said compressible material to atmosphere upon ambulation.

A common feature of some of the vacuum suspension systems described in the above patent publications is that the liner used in those systems is a cushion liner. Since a cushion liner and a socket into which it is inserted are closed at their distal end and open only at their proximal end, in order to suspend the socket and prosthetic limb from the residual limb it is only necessary to provide an airtight seal at the proximal mouth of the socket and liner, typically by overlapping the join between the residual limb, liner and socket with a sleeve. In contrast, when a locking liner is used the pin of the liner extends through the distal end of the socket. Since the distal seal of the socket is compromised by the pin passing through it, where a locking liner is used with a reduced pressure suspension system the airtight seal is achieved between the liner and the residual limb. Consequently any perforations in the liner will allow the passage of air between the liner and limb and compromise the suspension of the prosthetic limb from the residual limb. For this reason, there is technical prejudice against perforating locking liners, particularly at their distal end.

The present invention provides an improved reduced pressure prosthesis suspension system.

SUMMARY OF INVENTION

According to a first aspect of the invention, there is provided a sealing cap for a porous liner, the sealing cap comprising: a first portion comprising means for locating the sealing cap on a distal end of a said liner; a second portion which is resiliently deformable and movable between, a first position where the second portion is adapted to abut a corresponding portion of the said liner, and a second position where the second portion is adapted to be spaced from said corresponding portion of the said liner.

The means for locating the sealing cap on a distal end of the said liner may comprise means for preventing lateral movement of the sealing cap relative to the distal end of the said liner.

The means for locating the sealing cap on a distal end of the said liner may comprise a protrusion on one of the said liner and sealing cap and a cooperating recess on the other.

The said liner may comprise a boss and the means for locating the sealing cap on a distal end of the said liner may comprise a cooperating recess in the sealing cap.

The said liner may be a locking liner comprising a bore, the sealing cap comprising an aperture adapted to be in communication with the said bore and the means for locating the sealing cap on a distal end of the said locking liner may be a locking pin which is adapted to be fed through the aperture into the bore.

The second portion may be a skirt which may have a frusto-conical shape.

The first portion may comprise a frusto-conical part between the means for locating the sealing cap on a distal end of a said liner and the skirt.

The frusto-conical part of the first portion may have a thickness less than a thickness of the skirt.

According to a further aspect of the invention there is provided a prosthesis suspension system, comprising: a socket for receiving a residual limb and including mounting means for being mounted to a prosthetic limb; a liner having attachment means for attaching the liner to the socket; and a sealing cap as defined in any one of the preceding claims, wherein the sealing cap is adapted to be disposed between the locking liner and socket, the system further comprising a gap between the skirt of the sealing cap and an interior wall of the socket in which the second portion of the sealing cap is able to move between its first and second positions.

The attachment means for attaching the liner to the socket may be one or more of a locking pin, a vacuum source, a seal between the liner and the socket and a sleeve for sealing a proximal edge of the socket. The socket may have an expulsion port.

The liner may be perforated at its distal end where it is in contact with the skirt.

The liner may have an outer wicking layer and the distal end of the liner may be perforated where it is in contact with the first portion of the sealing cap.

BRIEF DESCRIPTION OF THE DRAWINGS

The present invention will now be described by way of example only, and with reference to the accompanying drawings in which.

DETAILED DESCRIPTION OF THE DRAWINGS

Figure 1:
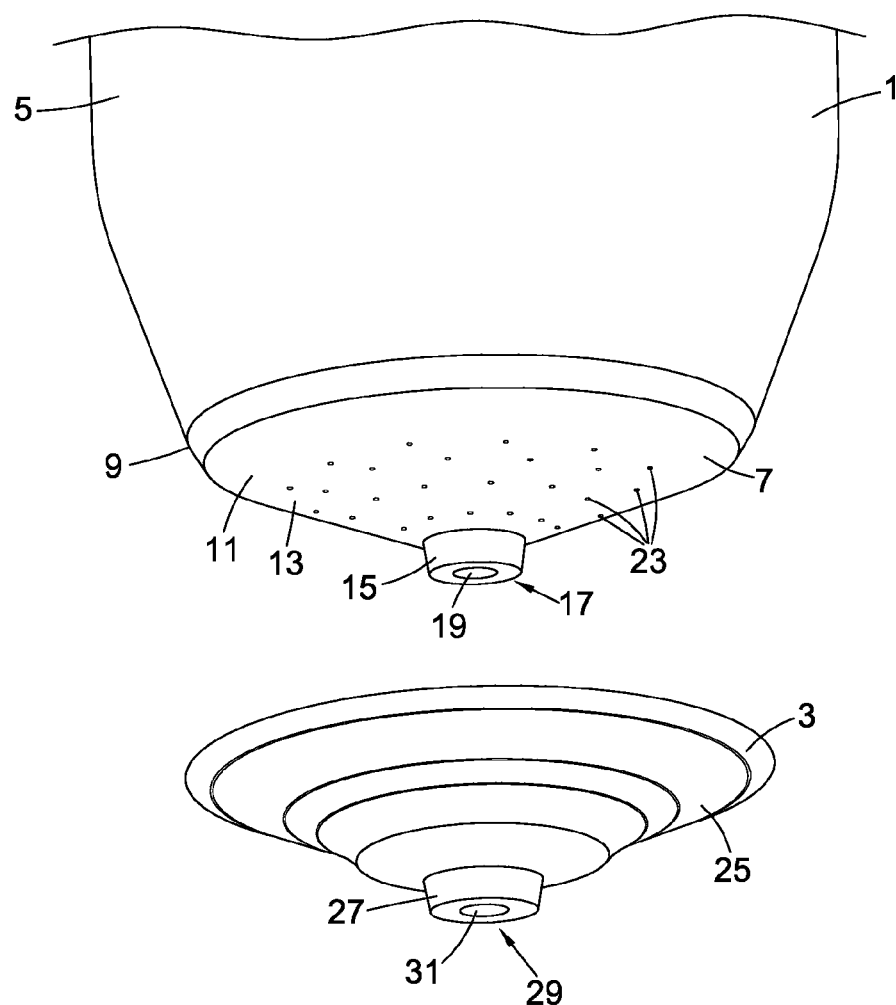
FIG. 1 is an exploded perspective view of a perforated liner and sealing cap forming part of the reduced pressure prosthesis suspension system in accordance with an embodiment of the invention.

FIG. 1 is an exploded perspective view of a distal portion of a perforated locking liner 1 and sealing cap 3 forming part of a reduced pressure prosthesis suspension system in accordance with an embodiment of the invention. As is renowned in the art, in addition to the liner 1 and cap 3 shown in FIG. 1, the system further includes a socket and locking pin, not shown in FIG. 1.

The perforated liner 1 comprises a flexible silicone body covered circumferentially with a fabric layer 5. An end cap 7 is fixed to a distal end 9 of the liner 1. An outer face 11 of the end cap 7 has a frusto-conical portion 13 with a boss 15 protruding distally from its centre 17. The boss 15 has a threaded bore 19 at its centre. The distal end 9 of the liner 1 is perforated, the perforations 23 passing through the end cap 7 and the silicone body. The density of the perforations 23 is around 5-10 perforations per square cm. The density of perforations 23 may be reduced where the perforations 23 pass through the body of an internal umbrella, so as not to adversely compromise the structural rigidity of the umbrella. Conversely, the density of perforations 23 may be greater where the perforations pass through fenestrations (through holes) in the umbrella. Furthermore, the number of perforations 23 per square cm may vary depending on mechanical properties (such as the resilience) of the material from which the liner 1 is made. The perforations 23 in use allow passage of air and sweat from the interior of the liner 1 to its exterior over an extended area of the residual limb. Other than the perforations 23 passing through the end cap 7 of the liner 1, the liner 1 is impermeable in a region immediately proximal to the end cap 7 so that the only permeable zone of a distal region of the liner 1 is through the end cap 7. The impermeable region of the line 1 may extend to a proximal rim of the liner or may extend around 10 cm in that direction, with a perforated or otherwise permeable region extending proximally to the impermeable region.

The sealing cap 3 has a similar overall shape to the end cap 7 of the liner, having a generally frusto-conical portion 25 with a boss 27 extending from its centre 29. The boss 27 has a smooth walled (unthreaded) central through bore 31. The sealing cap 3 is made from silicone- and may be made from other resiliently deformable material such as urethane, rubber or other materials having a hardness within the Shore A scale. A preferred feature of the material of the sealing cap 3 is that it is resistant to the slightly acidic properties of perspiration.

Figure 2:
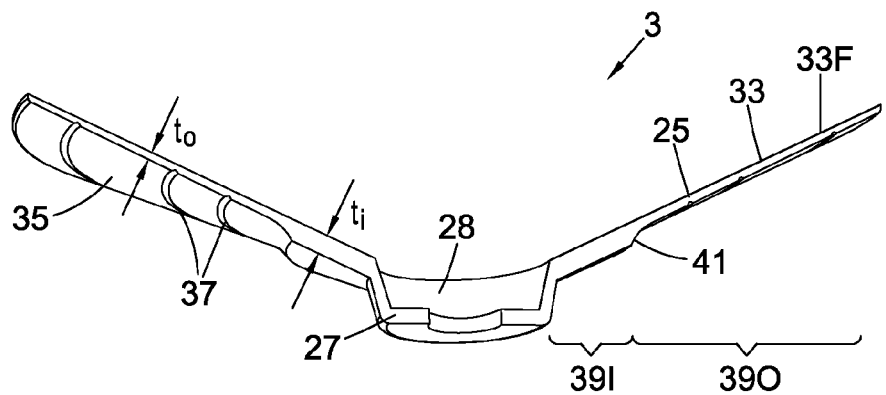
FIG. 2 is a sectional view of the sealing cap shown in FIG. 1 in accordance with an embodiment of the invention.
Figure 3:
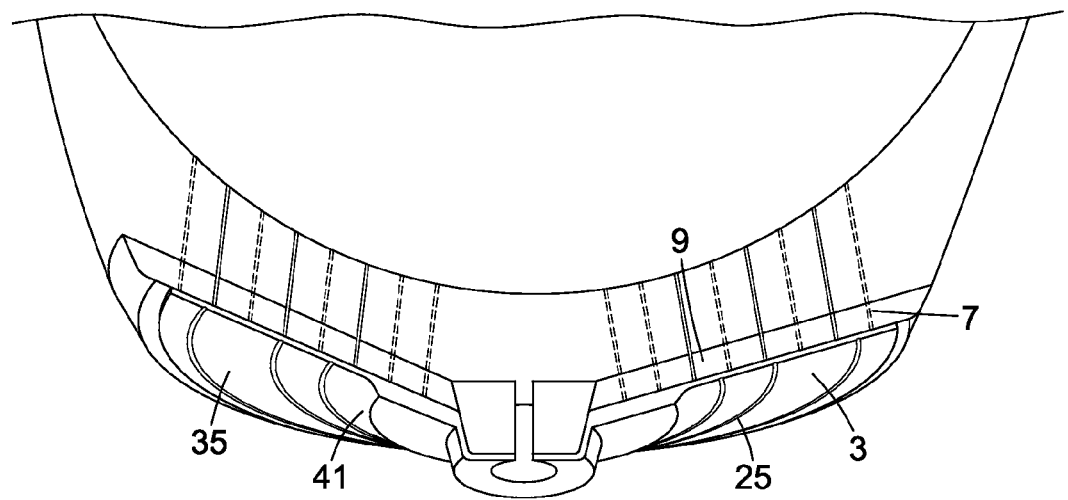
FIG. 3 is a sectional view of the perforated liner and sealing cap shown in FIG. 1 when the sealing cap is disposed on the liner.

The sealing cap 3 is shown in section in FIG. 2 and in FIG. 3 the sealing cap 3 is shown mounted on the distal end 9 of the liner 1. As can be seen in these Figures, the sealing cap 3 has a similar shape to the outer face 11 of the end cap 7. In particular the interior surface 33 of the sealing cap 3 is shaped to match the corresponding outer face 11 of the end cap 7. The interior surface 33 of the sealing cap 3 includes a boss recess 28 on the interior of the boss 27 which is shaped to fit over the boss 15 of the liner 1 such that the engagement of the boss 15 in the boss recess 28 locates the sealing cap 3 on the liner 1 by preventing relative lateral (left-right and in and out of the page as shown in the Figures) movement of these parts 1, 3.

The outer face 35 of the sealing cap 3 includes a plurality of concentric grooves or marks 37. The sole function of these grooves 37 is to assist cutting the sealing cap 3 to a required diameter. Since locking liners are supplied in different sizes the sealing cap 3 is manufactured having a diameter equal to or greater than the diameter of the largest supplied locking liner end cap and the grooves 37 are used as guides to aid a prosthetist or prosthetic technician in reducing the diameter of the sealing cap 3 to a suitable size. Alternatively sealing caps 3 without grooves or marks 37 and having different diameters may be manufactured, for example corresponding to the size of common liners.

The thickness of the sealing cap 3 differs between an inner circumferential band 39I of the frusto-conical portion 25 of the sealing cap 3 and an outer circumferential band 39O thereof. Whilst the interior surface 33F of the frusto-conical portion 25 of the sealing cap 3 has a generally frusto-conical shape, a step 41 is formed in the outer face 35 of the sealing cap 3 as the thickness of the sealing cap 3 transitions from a thickness $t_i$ of the inner circumferential band 39I of the frusto-conical portion 25 and a thickness $t_O$ of the outer circumferential band 39O of the frusto-conical portion 25, where $t_i > t_O$. The reduced thickness $t_O$ of the outer circumferential band 39O, referred to herein as the 'skirt' of the sealing cap 3, makes this portion more flexible than the inner circumferential band 39I of the frusto-conical portion 25. It will be apparent to the skilled person that whilst the 'full' thickness $t_i$ inner circumferential band 39I of the frusto-conical portion 25 is the load bearing portion, bearing the weight of the amputee, the reduced thickness $t_O$ of the outer circumferential band 39O of the frusto-conical portion 25 allows this portion of the sealing cap 3 to move when the liner 1 and sealing cap 3 are within a socket, as explained below. For convenience we herein define the functional parts of the sealing cap 3 as the boss 27 and the inner circumferential band 39I of the frusto-conical portion 25 together forming a first portion of the sealing cap 3 which, in use, is held against the end cap 7 of the liner 1 and the outer circumferential band 39O of the frusto-conical portion 25 of the sealing cap 3 can be defined as a second portion.

As is known in the art, a first step of producing a socket for a residuum is forming a cast around the residuum when a liner is donned thereon. When casting a socket for the liner 1 described above it is necessary to apply a casting gasket over the reduced thickness skirt 39O so that when the final socket is applied to the liner 1 and sealing cap 3 a cavity will exist between the skirt 39O of the sealing cap 3 and socket, as described below with reference to FIGS. 4A and 4B.

Figure 4A:
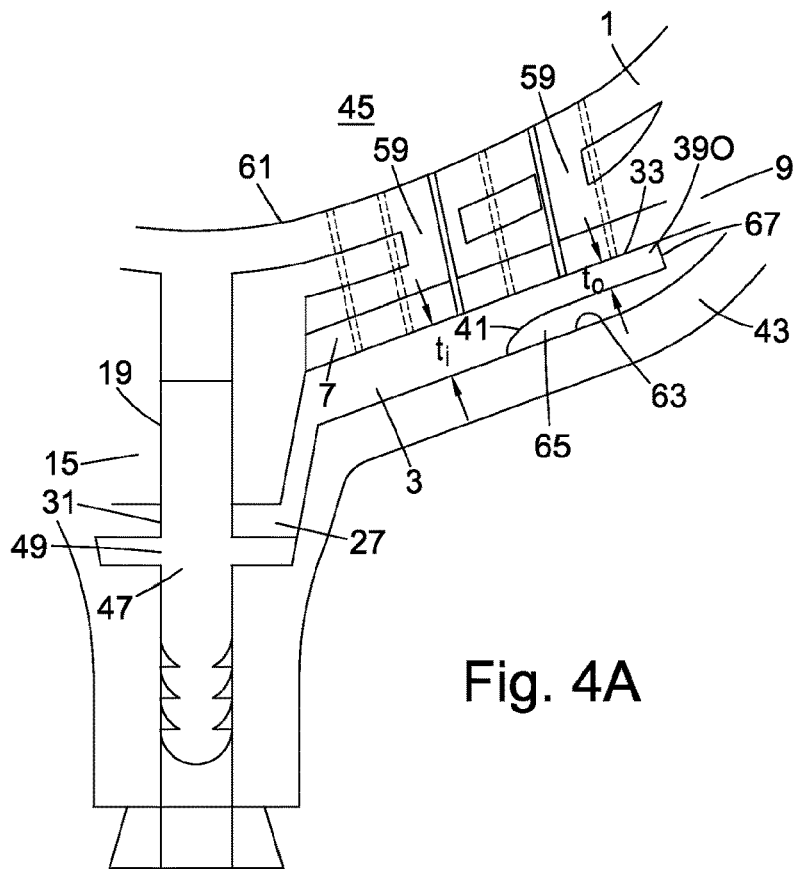
FIGS. 4A and 4B are partial sectional views of the prosthesis suspension system in the region of the sealing cap when a skirt thereof is in a first and second position respectively.
Figure 4B:
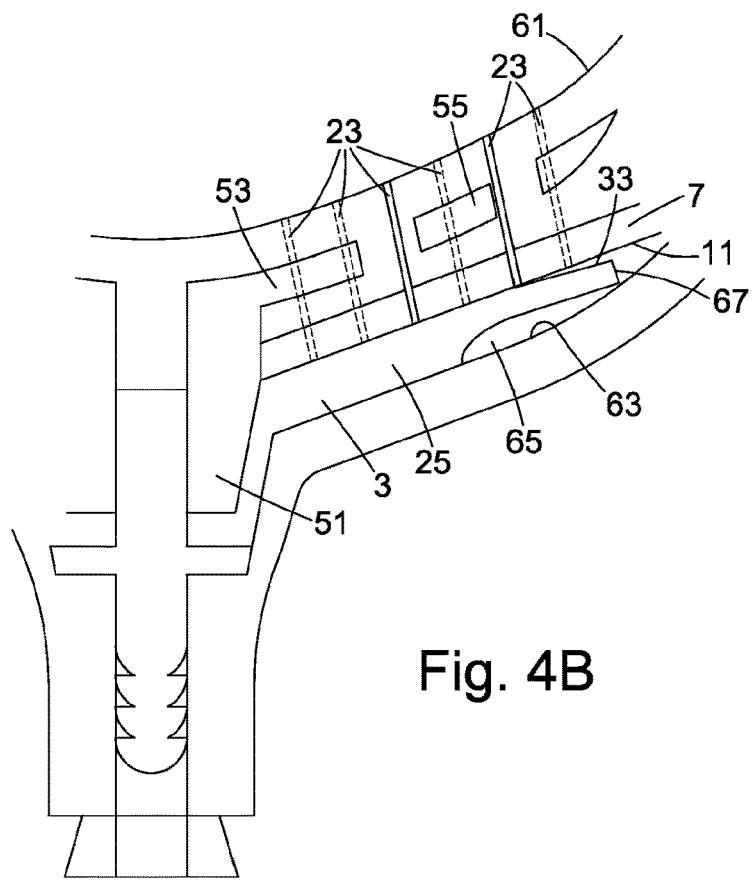

FIGS. 4A and 4B are close-up sectional views of the prosthesis suspension system comprising the sealing cap 3 and liner 1 in a socket 43, with the skirt 39O of the sealing cap 3 in alternative positions. As described in the Background to the Invention above, the socket 43 is made of a hard impermeable material that is shaped to fit a residual limb 45.

In FIG. 4A, the liner 1 has been donned on the residual limb 45 of an amputee, the sealing cap 3 has been positioned over the end cap 7 of the liner 1, and the resulting combination has been inserted into the socket 43. The liner 1 includes a locking pin 47 which is screwed into the threaded bore 19 of the boss 15 of the liner, through the bore 31 of the boss 27 of the sealing cap 3 and through an aperture 49 in the socket 43, forming an airtight seal between the cap 3, boss 15 and distal end 9 of the liner 1. As can be seen in FIGS. 4A and 4B, the bore 31 is formed in a central stem 51 of an umbrella 53 which forms part of the liner 1. In addition to the stem 51 at its centre, the umbrella 53 has a disc portion 55 which extends outwards from the central stem 51 and which is embedded in the silicone of the liner 1. The disc portion 55 of the umbrella 53 includes a number of through holes 59 which are filled with silicone and which help anchor the umbrella 53 within the silicone.

FIGS. 4A and 4B also show the perforations 23 which pass from the interior surface 61 of the liner 1 to the outer face 11 of the end cap 7 and which allow passage of air and sweat from the interior surface 61 to its exterior 11. The two perforations 23 which are shown in solid lines fall along the sectional line of these Figures and the perforations 23 shown in broken lines are behind that sectional line. The socket 43 may include a one-way expulsion valve (not shown), as is known in the art. Additionally or alternatively a vacuum device may be used to maintain a reduced pressure within the socket 43.

When the sealing cap 3 is sandwiched between the distal end 9 of the liner 1 and the interior surface 63 of the socket, a gap 65 exists between the sealing cap 3 and the interior surface 63 of the socket 43. This gap 65 is as a result of the reduced thickness to of the skirt 39O of the sealing cap 3 beyond the step 41. The gap 65 extends from the step 41 to beyond a peripheral edge 67 of the sealing cap 3, such that the skirt 39O is able to move away from the outer face 11 of the end cap 3 and into that gap 65. Since the skirt 39O is resiliently deformable, its "at rest" position is as shown in FIG. 4A, where it is in contact with the outer face 11 of the end cap 7.

In use, when the residual limb 45 is surrounded by the liner 1 any sweat which is secreted from the skin of the amputee will cover the inner surface 61 of the liner and if left there can act as a lubricant, causing relative movement between the liner and residual limb, leading to chafing and discomfort to the amputee. Since the liner 1 is perforated in the region of the end cap 7, any sweat, air or other fluid in that region is expelled through the perforations 23 when the residual limb 45 loads the inner wall 61 of the liner 1. This loading occurs whilst the amputee is standing and during the stance phase of the gait cycle when the residual limb 45 "pistons" within the liner 1. As sweat is forced though the perforations 23 it pushes against the inner surface 33 of the sealing cap 3 in the region of the outer circumferential band 39O of the frusto-conical portion 25 and this part of the skirt 39O will be pushed away from the outer face 11 of the end cap and the skirt 39O moves into the gap 65. The sweat makes its way over the peripheral edge 67 of the sealing cap 3 and gathers in the gap 65, from where it may drain out of the socket via the locking mechanism, or can be drawn away via a one way valve (if present), in either case optimally using an elevated vacuum source, such as a vacuum pump.

On completion of the stance phase of the gait cycle as the lower limb lifts off the ground the residual limb 45 will have a tendency to be drawn away from the interior surface 63 of the socket 43 in the region of the end cap 7. During this phase of the gait cycle sweat will no longer be pushed through the perforations 23 and due to the resilience in the skirt 39O of the sealing cap 3 the interior wall 33 of the sealing cap 3 will return to its 'at rest' position and once again seal against the outer face 11 of the end cap 7. In addition or alternatively, the lifting of the residual limb 45 will cause a reduced pressure or partial vacuum in this region. This partial vacuum will be transmitted via the perforations 23 to the interior wall 33 of the sealing cap 3 and pull this against the outer face 11 of the end cap 7, thereby sealing the sealing cap 3 against the end cap 7. By sealing the end cap 7 in this manner the sealing cap 3 helps maintain a reduced pressure within the liner 1 which supports suspension of the liner 1 and the rest of the prosthesis from the residual limb 45. In this manner, the combined action of the skirt 39O of the sealing cap 3 and the end cap 7 of the liner 1 function as a valve to maintain a reduced pressure within the cavity of the liner 1.

As the amputee continues to walk this process is repeated, with sweat being forced through the perforations 23 of the liner 1 during the stance phase when the distal end 9 of the liner 1 is compressed and with sealing cap 3 being drawn against the outer face 11 of the liner 1 to seal the liner 1 during the swing phase.

Various modifications will be apparent to those in the art and it is desired to include all such modifications as fall within the scope of the accompanying claims.

For example, the body of the liner 1 in FIGS. 1-4B is made of impermeable silicone which is perforated at the distal end 21 of the liner 1. Whilst silicone is an impermeable material which in those Figures is perforated to make the liner 1 porous, instead of using silicone at the distal end 9 of the liner this part of the liner may be made from a porous material, such as a sintered material or fabric such as Gore-Tex(®), which does not need to be perforated to allow passage of air and moisture from the inside to the outside of the liner 1.

Since the displaceable skirt 39O of the sealing cap 3 is only in communication with peripheral perforations 23 in the distal end 21 of the liner 1 (i.e., those which are distal to the centre 17 of the end cap 7) the perforations 23 which are proximal to the centre 17 of the end cap may, in practice, be permanently sealed, since the inner surface 33 of the inner circumferential band 39I of the frusto-conical portion 25 of the sealing cap 3 permanently abuts that portion of the end cap. This may lead to a build-up of moisture on the interior surface 61 of the liner 1 towards its axial centre. To address this situation an inner portion of the outer face 11 of the end cap 7 may be covered by a porous membrane, such as a fabric layer. The fabric layer will act as a wicking/transmission layer and allow sweat to be pushed from the interior surface 61 of the liner 1, through the inner perforations 23 and along the fabric layer to the peripheral edge 67 of the sealing cap 3. In order to allow the sealing cap 3 to function as a valve by sealing against the outer face 11 of the end cap 7, an outer circumferential band of the outer face 11 of the end cap 7 should be free from a porous covering, so that when it is in contact with the corresponding part of the sealing cap 3 it provides a seal.

In the embodiments described above the sealing cap 3 is a separate piece from the locking liner. In other embodiments the sealing cap may be permanently fixed to the distal end of the locking liner. For example, the sealing cap may be glued or otherwise bonded to the locking liner when the two parts are first mated. Alternatively the sealing cap may be integrally formed on the end cap of the locking liner. If the sealing cap is fixed to the locking liner it would be joined in the region of the boss 15 of the liner so that the skirt 39O is free to move away from and back towards the end face 11 of the locking liner 1, so as to provide the valve functionality.

In the embodiment described above, the thickness of the sealing cap 3 transitions from a thickness $t_i$ of the inner circumferential band 39I of the frusto-conical portion 25 to a thickness $t_O$ of the outer circumferential band 39O of the frusto-conical portion 25, where $t_i > t_O$. In other embodiments the thickness of the frusto-conical portion 25 may be constant as it extends outwards from the boss 27 or it may decrease gently, without having a step 41. In such embodiments the ability of the outer circumferential band 39O to move as a valve may be provided by having a step in one or both of the end cap 7 of the liner 1 and in the interior wall 63 of the socket, thereby defining a gap in which the outer circumferential band 39O may reciprocate.

Whilst the embodiment described with reference to the Figures uses a locking liner and locking pin, the invention can also be embodied in a cushion (non-locking) liner. To achieve this the cushion liner and sealing cap will need to be adapted to locate the sealing cap on the distal end of the liner in such a manner where lateral movement of these parts is inhibited. Whilst the embodiment shown in the Figures uses a boss 15 on the liner and a cooperating recess 28 on the sealing cap 3, since a cushion liner does not typically include a boss, other mechanical interfaces can be used to locate the sealing cap on the distal end of the cushion liner. These mechanical interfaces may comprise a protrusion on one of the liner and the sealing cap and a cooperating recess on the other of the liner and the sealing cap. Alternatively other locating means can be used such as hook and loop fastener, other mechanical engagements or magnets.

In the embodiment described above, the different thicknesses $t_i$, $t_O$ of the sealing cap 3 are provided by the inner circumferential band 39I and the outer circumferential band 39O of the frusto-conical portion 25. Since the function of the full thickness $t_i$ portion is to bear the load of the amputee and the function of the reduced thickness $t_O$ portion is to allow that portion of the sealing cap 3 to move away from and back towards the end cap 7 of the liner 1, the full thickness $t_i$ portion and the reduced thickness $t_O$ portion can be arranged other than concentrically. For example the outer circumferential band may be of full thickness and the inner circumferential band may be of a reduced thickness, so that the inner circumferential band moves away from and back towards the liner end cap 7 during the gait cycle. According to this arrangement the inner circumferential band would include perforations or other holes or slits to allow passage of sweat etc. from the interior surface 31 of the sealing cap 3 to the interior surface 61 of the socket 43. These holes or slits would not be aligned with the perforations 23 of the liner 1, so that the inner circumferential band will seal against the liner end cap 7 when abutted thereto. Alternatively the full thickness portions may be formed as radially extending spines with reduced thickness portions therebetween.

The sealing cap 3 described above is disposed on the distal end 9 of the liner 1. In other embodiments a sealing cap or flap may be disposed at a different position of the liner 1 corresponding to a perforated portion of the liner 1. For example, if a side wall of the liner 1 is perforated instead of or in addition to the distal end 9 of the liner, the sealing cap would have a portion which is movable between a first position (where it is adapted to abut the perforated portion of the liner) and a second position (where it adapted to be spaced from that portion of the liner) in accordance with the invention. As described above the sealing cap or flap may be a separate piece from the liner or permanently attached thereto.

In our earlier patent application published as US-A-2012/191218, the contents of which are incorporated herein by reference, we describe a vacuum-assisted suspension device for a lower limb prosthesis which secures the prosthesis to a residual body portion. FIG. 8D of that publication describes the use of voids 104V in a surface of a pad 104. The voids 104V are open to the surface 104O of the pad 104 and have a blind end in the body of the pad 104. The voids 104V assist in evacuating air from between the socket and the stump, as described in that publication, when the pad 104 is repeatedly compressed. Similarly voids may be incorporated in one or both of the end cap 7 of the perforated liner 1 and the sealing cap 3, with the voids being open to the outer face 11 of the end cap 7 and the interior surface 33 of the sealing cap respectively. Similarly, other voids as described in that publication can be used to enhance the vacuum between the end cap 7 and the sealing cap 3.

What is claimed is:

1. A prosthesis liner system comprising:
a porous prosthesis liner having a perforated distal end, and
a valve for said porous prosthesis liner, the valve comprising:
a first portion comprising:
means for locating the valve on the distal end of the porous prosthesis liner; and
a frusto-conical shaped inner circumferential band having a first thickness; and
a second portion extending from the first portion of the valve to a peripheral edge of the valve, the second portion comprising a frusto-conical shaped outer circumferential band having a second thickness which is not equal to the first thickness, thereby resulting one of the inner and outer circumferential bands being a thinner circumferential band and the other one of the inner and outer circumferential bands being a thicker circumferential band,
wherein the thinner circumferential band is resiliently deformable and movable between:
a first, at rest, position where the thinner circumferential band is adapted to abut a corresponding portion of the distal end of said porous prosthesis liner, and
a second position where the thinner circumferential band is adapted to be spaced from said corresponding portion of the distal end of said porous prosthesis liner,
wherein the means for locating the valve on a distal end of the said porous prosthesis liner comprises means for preventing lateral movement of the valve relative to the distal end of the said porous prosthesis liner.

2. The prosthesis liner system as claimed in claim 1, wherein the means for locating the valve on a distal end of said porous prosthesis liner comprises a protrusion on one of said porous prosthesis liner and the valve and a cooperating recess on the other.

3. The prosthesis liner system as claimed in claim 1, wherein said porous prosthesis liner comprises a boss and the means for locating the valve on a distal end of said porous prosthesis liner comprises a cooperating recess in the valve.

4. The prosthesis liner system as claimed in claim 1, wherein said porous prosthesis liner comprises a bore, the valve comprises an aperture adapted to be in communication with said bore and the means for locating the valve on a distal end of said porous prosthesis liner is a locking pin which is adapted to be fed through the aperture into the bore.

5. The prosthesis liner system as claimed in claim 1, wherein the first thickness is greater than the second thickness.

6. The prosthesis liner system as claimed in claim 1, wherein the first thickness is less than the second thickness.

7. The prosthesis liner system as claimed in claim 1, further comprising:
a socket for receiving a residual limb and including mounting means for being mounted to a prosthetic limb;
wherein the porous prosthesis liner includes attachment means for attaching the porous prosthesis liner to the socket; and
wherein the valve is adapted to be disposed between the porous prosthesis liner and the socket,
the system further comprising a gap between the thinner circumferential band of the valve and an interior wall of the socket into which the thinner circumferential band of the valve is able to move between its first and second positions,
wherein the perforations in the porous prosthesis liner at its distal end are where it is in contact with the thinner circumferential band.

8. The prosthesis liner system as claimed in claim 7, wherein the attachment means for attaching the porous prosthesis liner to the socket is one or more of a locking pin, a vacuum source, a seal between the porous prosthesis liner and the socket and a sleeve for sealing a proximal edge of the socket.

9. The prosthesis liner system as claimed in claim 7, wherein the socket has an expulsion port.

10. The prosthesis liner system as claimed in claim 7, wherein the porous prosthesis liner has an outer wicking layer.

* * * * *